(12) United States Patent
Blacker

(10) Patent No.: US 11,413,431 B2
(45) Date of Patent: *Aug. 16, 2022

(54) HEMOSTASIS VALVE FOR GUIDE CATHETER CONTROL

(71) Applicant: Corindus, Inc., Waltham, MA (US)

(72) Inventor: Steven J. Blacker, Framingham, MA (US)

(73) Assignee: Corindus, Inc., Newton, MA (US)

( * ) Notice: Subject to any disclaimer, the term of this patent is extended or adjusted under 35 U.S.C. 154(b) by 233 days.

This patent is subject to a terminal disclaimer.

(21) Appl. No.: 16/388,181

(22) Filed: Apr. 18, 2019

(65) Prior Publication Data

US 2020/0016371 A1 Jan. 16, 2020

Related U.S. Application Data

(63) Continuation of application No. 15/252,561, filed on Aug. 31, 2016, now Pat. No. 10,307,570, which is a
(Continued)

(51) Int. Cl.
*A61M 25/01* (2006.01)
*A61M 25/06* (2006.01)
*A61M 39/06* (2006.01)
*A61M 25/00* (2006.01)
*A61B 34/30* (2016.01)
(Continued)

(52) U.S. Cl.
CPC ......... *A61M 25/0147* (2013.01); *A61B 34/30* (2016.02); *A61M 25/0075* (2013.01); *A61M 25/0116* (2013.01); *A61M 25/02* (2013.01);

*A61M 25/065* (2013.01); *A61M 25/09* (2013.01); *A61M 39/06* (2013.01); *A61B 1/00133* (2013.01); *A61B 2034/301* (2016.02)

(58) Field of Classification Search
CPC .......... A61B 1/00133; A61B 2034/301; A61B 34/30; A61M 25/0116; A61M 25/0147; A61M 25/02; A61M 25/065; A61M 25/09; A61M 39/06; A61M 25/0075
See application file for complete search history.

(56) References Cited

U.S. PATENT DOCUMENTS

| 4,397,091 A | 8/1983 | Gustavsson et al. |
| 4,795,434 A | 1/1989 | Kujawski |

(Continued)

FOREIGN PATENT DOCUMENTS

| CN | 101909688 | 12/2010 |
| CN | 104622579 | 1/2017 |

(Continued)

OTHER PUBLICATIONS

Extended European Search Report dated Feb. 16, 2017 in Application No. EP 10754060.1.
(Continued)

*Primary Examiner* — Quynh-Nhu H. Vu

(57) ABSTRACT

An extension member is has a body with a proximal end and an opposing distal end. It includes a hollow lumen extending therethrough from the proximal end to the distal end. It has a female luer lock connector proximate its proximal end and a male luer lock connector proximate its distal end. Its body has an outer surface with a driven member.

18 Claims, 12 Drawing Sheets

Related U.S. Application Data continuation of application No. 14/020,487, filed on Sep. 6, 2013, now Pat. No. 9,452,277.

(60) Provisional application No. 61/832,227, filed on Jun. 7, 2013, provisional application No. 61/699,711, filed on Sep. 11, 2012, provisional application No. 61/697,734, filed on Sep. 6, 2012.

(51) Int. Cl.
*A61M 25/02* (2006.01)
*A61M 25/09* (2006.01)
*A61B 1/00* (2006.01)

(56) References Cited

U.S. PATENT DOCUMENTS

| | | |
|---|---|---|
| 5,057,093 A | 10/1991 | Clegg et al. |
| 5,133,364 A | 7/1992 | Palermo et al. |
| 5,267,983 A | 12/1993 | Oilschlager et al. |
| 5,273,546 A | 12/1993 | McLaughlin et al. |
| 5,288,556 A | 2/1994 | Lemelson |
| 5,315,737 A | 5/1994 | Ouimet |
| 5,324,271 A * | 6/1994 | Abiuso ............ A61M 39/0613 604/167.03 |
| 5,338,314 A | 8/1994 | Ryan |
| 5,352,215 A | 10/1994 | Thome et al. |
| 5,366,464 A | 11/1994 | Belknap |
| 5,578,014 A | 11/1996 | Erez et al. |
| 5,599,327 A * | 2/1997 | Sugahara ......... A61M 39/0613 604/539 |
| 5,882,333 A | 3/1999 | Schaer et al. |
| 5,911,710 A * | 6/1999 | Barry ............... A61M 39/0693 604/167.04 |
| 5,993,422 A | 11/1999 | Schafer |
| 6,004,271 A | 12/1999 | Moore |
| 6,086,008 A | 7/2000 | Gray et al. |
| 6,193,735 B1 | 2/2001 | Stevens |
| 6,197,016 B1 | 3/2001 | Fourkas et al. |
| 6,292,681 B1 | 9/2001 | Moore |
| 6,726,675 B1 | 4/2004 | Beyer |
| 6,743,210 B2 | 6/2004 | Hart et al. |
| 6,814,727 B2 | 11/2004 | Mansouri-Ruiz |
| 7,118,582 B1 | 10/2006 | Wang et al. |
| 7,335,182 B1 * | 2/2008 | Hilaire .............. A61M 39/06 604/27 |
| 7,449,002 B1 | 11/2008 | Wenstad |
| 7,670,328 B2 | 3/2010 | Miller |
| 7,686,816 B2 | 3/2010 | Belef et al. |
| 7,867,241 B2 | 1/2011 | Brock et al. |
| 7,887,549 B2 | 2/2011 | Wenderow et al. |
| 7,905,828 B2 | 3/2011 | Brock et al. |
| 7,922,693 B2 | 4/2011 | Reis |
| 7,938,851 B2 | 5/2011 | Olson et al. |
| 7,963,288 B2 | 6/2011 | Rosenberg et al. |
| 7,998,020 B2 | 8/2011 | Kidd et al. |
| 8,092,397 B2 | 1/2012 | Wallace et al. |
| 8,108,069 B2 | 1/2012 | Stahler et al. |
| 8,114,032 B2 | 2/2012 | Ferry et al. |
| 8,202,244 B2 | 6/2012 | Cohen et al. |
| 8,409,234 B2 | 4/2013 | Stahler et al. |
| 8,425,465 B2 | 4/2013 | Nagano et al. |
| 8,480,618 B2 | 7/2013 | Wenderow et al. |
| 8,777,931 B2 * | 7/2014 | Davis ................ A61M 39/10 285/332 |
| 8,790,297 B2 | 7/2014 | Bromander et al. |
| 8,926,529 B2 | 1/2015 | Rollins et al. |
| 9,452,277 B2 * | 9/2016 | Blacker ............ A61M 25/0116 |
| 9,814,864 B2 | 11/2017 | Scarpine et al. |
| 10,441,374 B2 | 10/2019 | Tavallaei et al. |
| 2002/0165536 A1 | 11/2002 | Bjorklund et al. |
| 2004/0064086 A1 | 4/2004 | Gottlieb et al. |
| 2004/0068173 A1 | 4/2004 | Viswanathan |
| 2004/0172008 A1 | 9/2004 | Layer |
| 2005/0203382 A1 | 9/2005 | Govari et al. |
| 2005/0222554 A1 | 10/2005 | Wallace et al. |
| 2005/0272976 A1 * | 12/2005 | Tanaka ............... A61B 1/0016 600/114 |
| 2007/0060879 A1 | 3/2007 | Weitzner et al. |
| 2007/0123070 A1 | 5/2007 | Bencteux |
| 2007/0239106 A1 | 10/2007 | Weitzner et al. |
| 2008/0004600 A1 * | 1/2008 | Kitani ................ A61M 39/10 604/533 |
| 2008/0051820 A1 | 2/2008 | Gong et al. |
| 2008/0300592 A1 | 12/2008 | Weitzner et al. |
| 2008/0319387 A1 | 12/2008 | Amisar et al. |
| 2009/0247993 A1 | 10/2009 | Kirschenman et al. |
| 2010/0036329 A1 * | 2/2010 | Razack ............ A61M 39/0613 604/256 |
| 2010/0069833 A1 | 3/2010 | Wenderow et al. |
| 2010/0130987 A1 | 5/2010 | Wenderow et al. |
| 2010/0204646 A1 | 8/2010 | Plicchi et al. |
| 2010/0274078 A1 | 10/2010 | Kim et al. |
| 2010/0318101 A1 * | 12/2010 | Choi .................. A61B 34/30 606/130 |
| 2011/0028894 A1 | 2/2011 | Foley et al. |
| 2011/0105954 A1 | 5/2011 | Cohen et al. |
| 2011/0166513 A1 | 7/2011 | Cohen et al. |
| 2011/0264038 A1 | 10/2011 | Fujimoto et al. |
| 2012/0078080 A1 | 3/2012 | Foley et al. |
| 2012/0132450 A1 | 5/2012 | Timm et al. |
| 2012/0179032 A1 | 7/2012 | Bromander et al. |
| 2012/0179167 A1 | 7/2012 | Wenderow et al. |
| 2012/0184803 A1 | 7/2012 | Simon et al. |
| 2012/0184955 A1 | 7/2012 | Pivotto et al. |
| 2012/0220931 A1 | 8/2012 | Cohen et al. |
| 2013/0041360 A1 * | 2/2013 | Farritor ............ A61B 18/1445 606/29 |
| 2014/0001234 A1 * | 1/2014 | Shelton, IV ........ A61B 17/068 74/25 |
| 2014/0066690 A1 | 3/2014 | Blacker |
| 2015/0090057 A1 | 4/2015 | Pacheco et al. |
| 2018/0168751 A1 | 6/2018 | Yi et al. |

FOREIGN PATENT DOCUMENTS

| | | |
|---|---|---|
| EP | 0566426 A1 | 10/1993 |
| EP | 970663 | 1/2000 |
| JP | 2005143647 | 6/2005 |
| JP | 2005523125 | 8/2005 |
| WO | 0009020 | 2/2000 |
| WO | 2005117688 A2 | 12/2005 |
| WO | 2005117688 A3 | 3/2006 |
| WO | 2012037213 A1 | 3/2012 |
| WO | 2012088201 A3 | 8/2012 |
| WO | 2013043804 A1 | 3/2013 |
| WO | 2013043872 A1 | 3/2013 |

OTHER PUBLICATIONS

Exam Report for EP 13835435.2; dated Mar. 14, 2018; 7 pages.
Extended European Search Report for EP 13835435.2; dated Sep. 21, 2016; 8 pages.
PCT International Search Report and Written Opinion for Application No. PCT/US2013/058536; dated Dec. 12, 2013; 11 pages.
EESR for EP 19189906.1; dated Nov. 6, 2019; 8 pages.

* cited by examiner

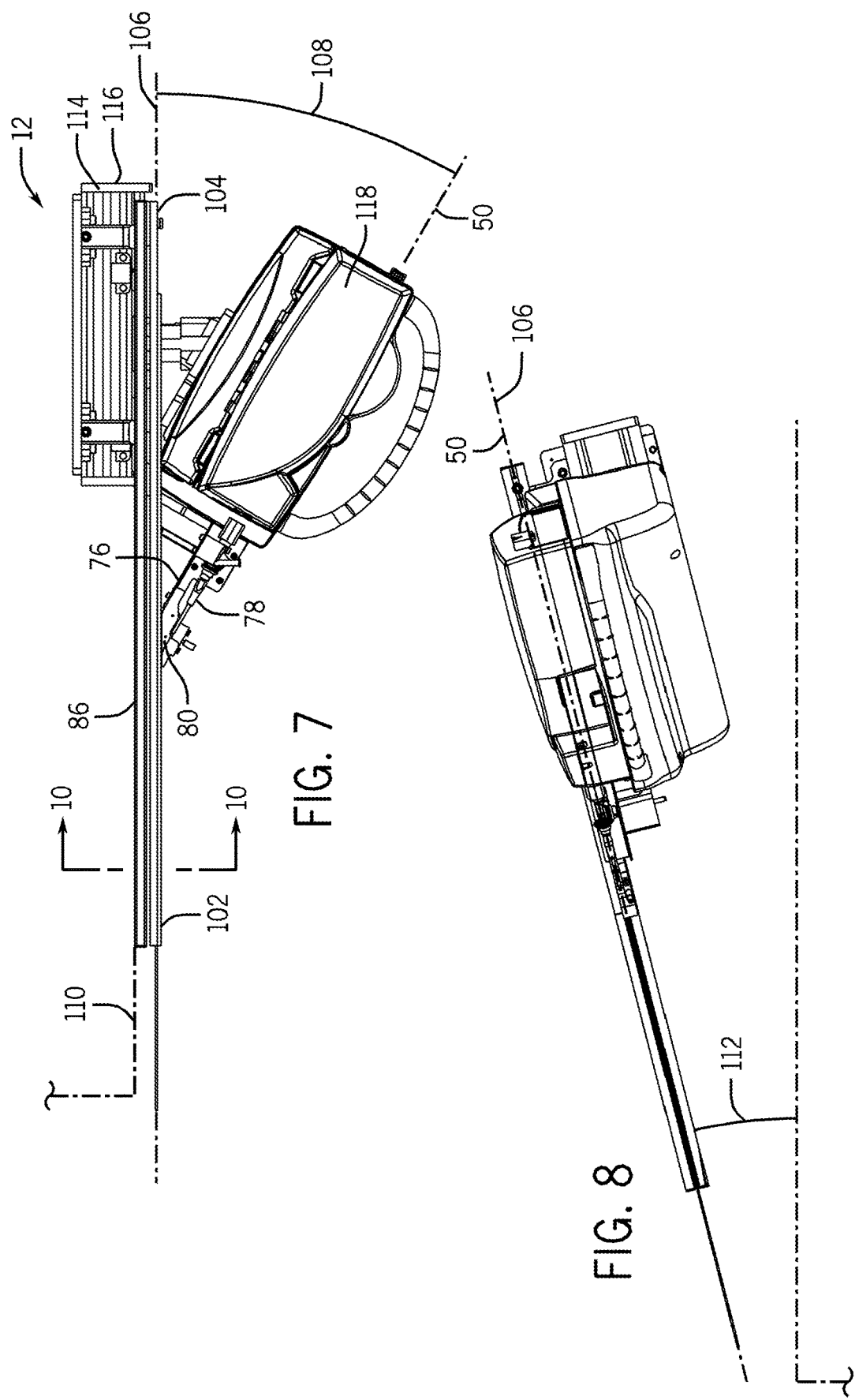

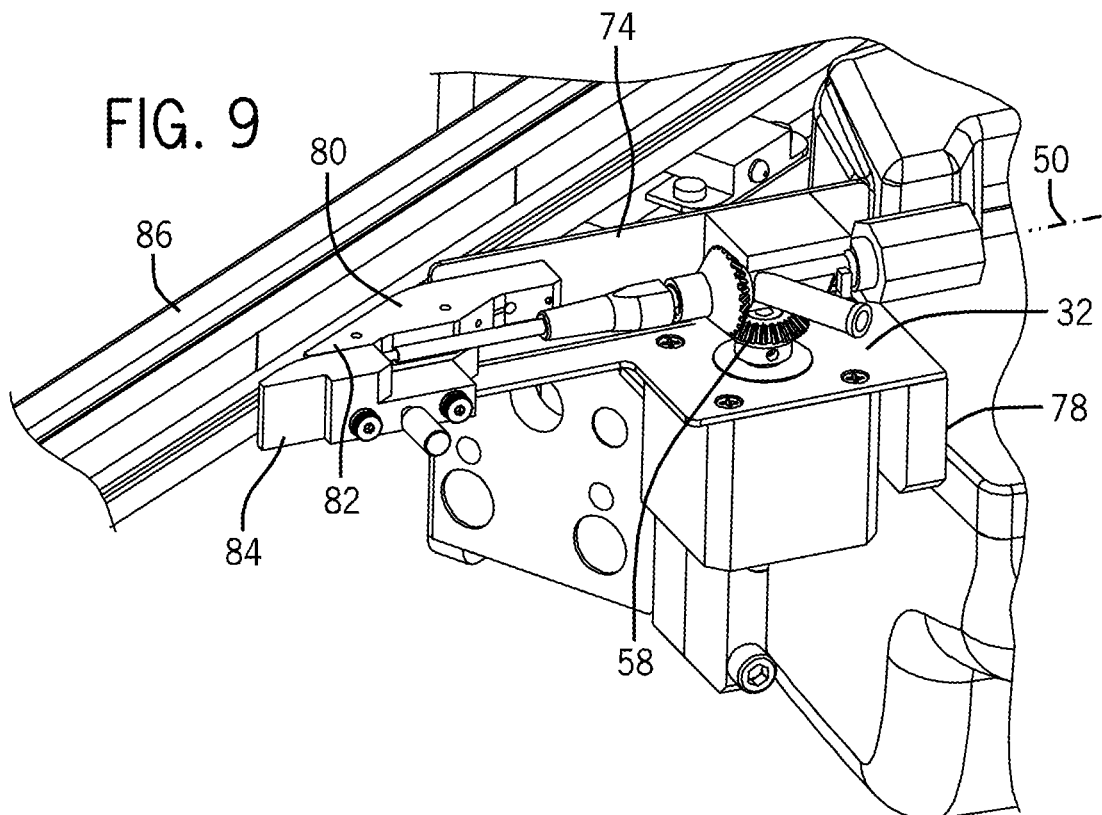

HEMOSTASIS VALVE FOR GUIDE CATHETER CONTROL

CROSS-REFERENCE TO RELATED PATENT APPLICATIONS

This application is a continuation of U.S. application Ser. No. 15/252,561, filed Aug. 31, 2016, entitled "HEMOSTASIS VALVE FOR GUIDE CATHETER CONTROL" which is a continuation of U.S. application Ser. No. 14/020,487, filed Sep. 6, 2013, entitled "HEMOSTASIS VALVE FOR GUIDE CATHETER CONTROL", which claims the benefit of U.S. Provisional Application No. 61/832,227, filed Jun. 7, 2013, entitled "GUIDE CATHETER DRIVE", and U.S. Provisional Application No. 61/699,711, filed Sep. 11, 2012, entitled "HEMOSTASIS VALVE AND SYSTEM FOR GUIDE CATHETER CONTROL" and U.S. Provisional Application No. 61/697,734, filed Sep. 6, 2012, entitled "HEMOSTASIS VALVE FOR GUIDE CATHETER CONTROL", all of which are incorporated herein by reference in their entireties.

BACKGROUND

The present invention relates generally to the field of catheter systems for performing diagnostic and/or intervention procedures. The present invention relates specifically to a hemostasis valve for guide catheter control in robotic catheter system.

Vascular disease, and in particular cardiovascular disease, may be treated in a variety of ways. Surgery, such as cardiac bypass surgery, is one method for treating cardiovascular disease. However, under certain circumstances, vascular disease may be treated with a catheter based intervention procedure, such as angioplasty. Catheter based intervention procedures are generally considered less invasive than surgery.

During one type of intervention procedure, a guide catheter is inserted into a patient's femoral artery and positioned proximate the coronary ostium of a patient's heart. A guide wire is inserted into the guide catheter typically through a hemostasis valve and maneuvered through the patient's arterial system until the guide wire reaches the site of the lesion. A working catheter is then moved along the guide wire until the working catheter such as a balloon and stent are positioned proximate the lesion to open a blockage to allow for an increased flow of blood proximate the lesion. In addition to cardiovascular disease, other diseases may be treated with catheterization procedures.

SUMMARY OF THE INVENTION

In one embodiment a hemostasis valve is provided which has a valve body with a first and second leg. The first leg has a proximal port, a distal port and a lumen extending between the proximal port and the distal port. At least one valve is located in the lumen adjacent the proximal port to permit an interventional device to be passed therethrough. The second leg extends at an angle relative to the first leg and is in fluid communication with the first leg. A rotating male luer lock connector is rotatably connected to the first leg proximate to the distal port and is configured to secure a guide catheter thereto. The rotating male luer lock connector has a driven member configured to be rotatably driven by a drive mechanism. The rotating male luer lock connector is rotatingly coupled with the guide catheter.

In another embodiment a combined hemostasis valve and extension member is provided. The hemostasis valve has a valve body with a first and second leg. The first leg has a proximal port, a distal port and a lumen extending between the proximal port and the distal port. At least one valve is located in the lumen adjacent the proximal port to permit an interventional device to be passed therethrough. The second leg extends at an angle relative to the first leg and is in fluid communication with the first leg. A rotating male luer lock connector is rotatably connected to the first leg proximate to the distal port. The extension member has a proximal end coupled to the rotating male luer lock connector and a distal end configured to secure a guide catheter thereto. It also has a driven member configured to be rotatably driven by a drive mechanism.

In a further embodiment an extension member is additionally provided that has a body with a proximal end and an opposing distal end. It includes a hollow lumen extending therethrough from the proximal end to the distal end. It has a female luer lock connector proximate its proximal end and a male luer lock connector proximate its distal end. Its body has an outer surface with a driven member.

BRIEF DESCRIPTION OF THE DRAWINGS

FIG. 7 is a top view of the catheter bedside system of FIG. 2.

FIG. 8 is a side view of the catheter bedside system of FIG. 2.

FIG. 9 is an isometric view of the guide catheter drive mechanism and track.

FIG. 10 is a cross sectional view of the track.

DETAILED DESCRIPTION OF THE EXAMPLE EMBODIMENTS

Figure 1:
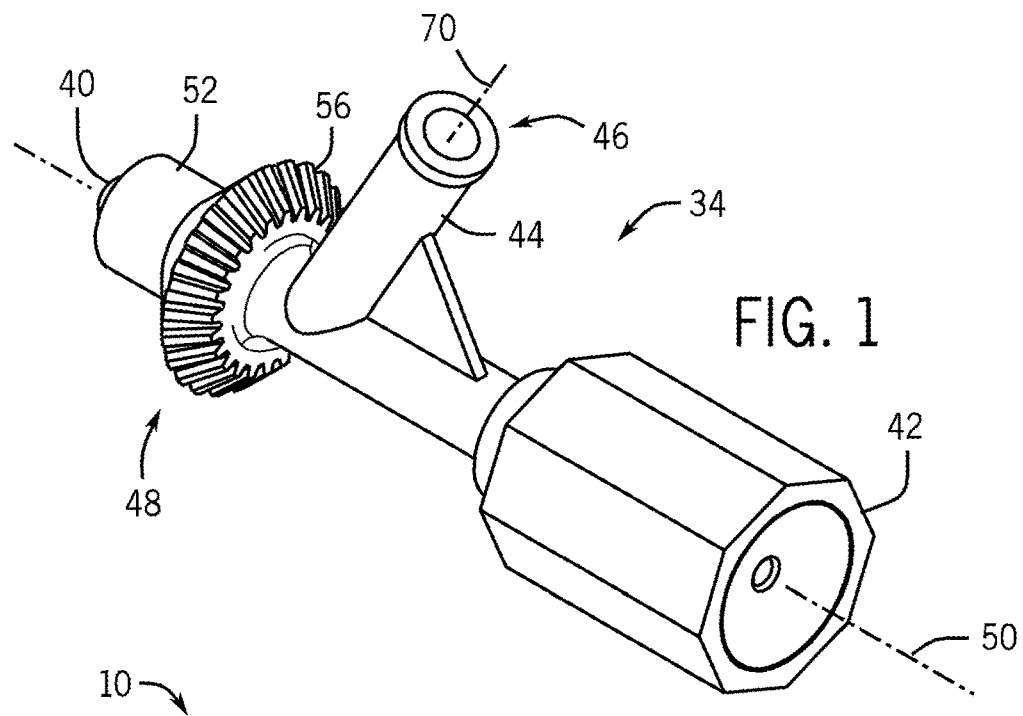
FIG. 1 is an isometric view of a hemostasis valve.

Referring to FIG. 1, a Y-connector or hemostasis valve 34 includes a valve body with a first leg 38 having a proximal port adjacent a proximal end 42 and a distal port adjacent a distal end 40. First leg 38 includes lumen extending between the proximal end 42 and the distal end 40. A valve 162 is disposed adjacent proximal end 42. A rotating luer connector 48 is rotatably secured to first leg 38 proximate distal end 40. Rotating luer connector 48 includes a member 56 configured to be rotatably driven by a drive mechanism of a robotic catheter system 10.

Figure 2:
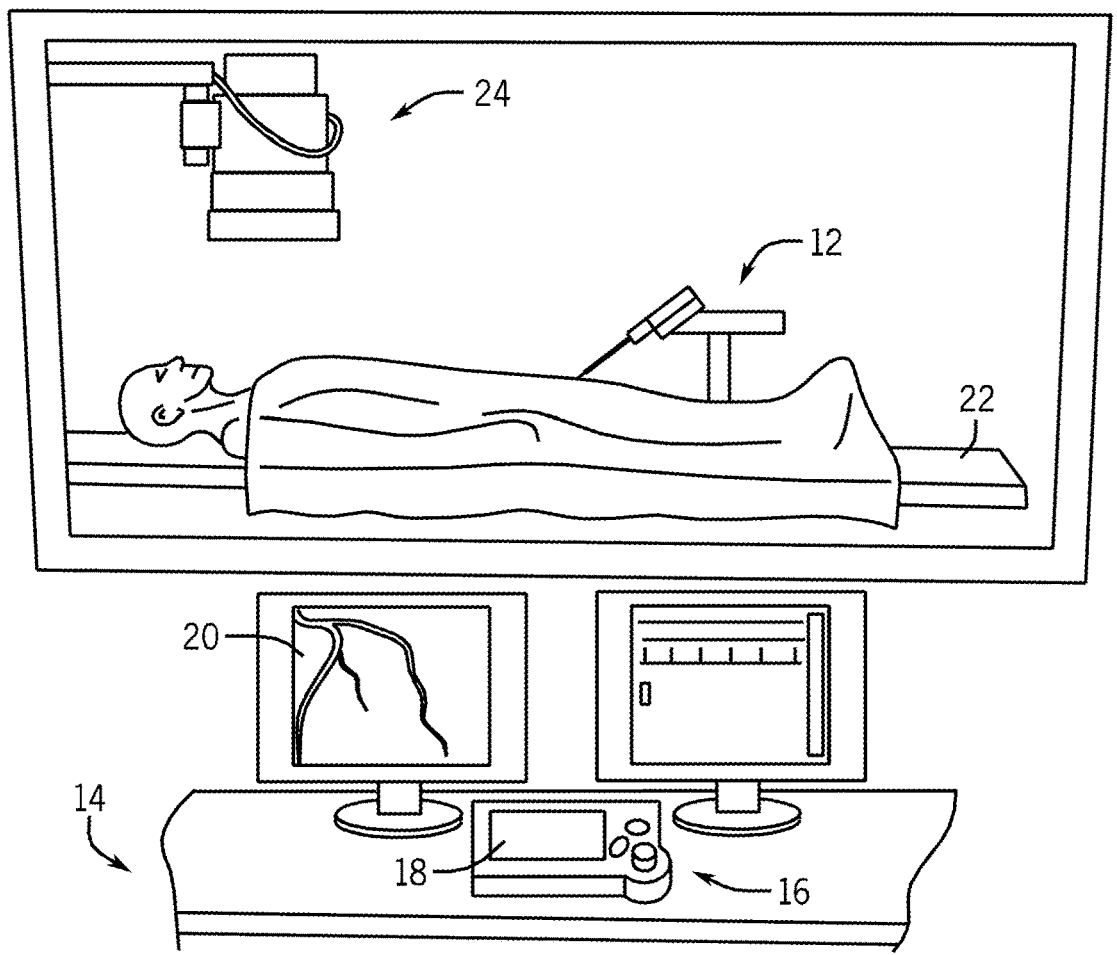
FIG. 2 is a schematic view of a robotic catheter control system.

Referring to FIG. 2, a robotic catheter system 10 includes a bedside system 12, a work station 14 including a controller 16, a user interface 18 and display 20. Bedside system 12 is located adjacent a patient bed 22 and an imaging system 24. Imaging system 24 may be any medical imaging system that may be used in conjunction with a catheter based medical procedure (e.g., non-digital x-ray, digital x-ray, CT, MRI, ultrasound, etc.).

In one embodiment, imaging system 24 is a digital x-ray imaging device that is in communication with workstation 14. Imaging system 24 is configured to take x-ray images of the appropriate area of patient during a particular procedure. For example, imaging system 24 may be configured to take one or more x-ray images of the heart to diagnose a heart condition. Imaging system 24 may also be configured to take one or more x-ray images during a catheter based medical procedure (e.g., real-time images) to assist the user of workstation 14 to properly position a guide wire, guide catheter, and a working catheter such as a stent during a procedure. The image or images may be displayed on display 20 to allow the user to accurately steer a distal tip of a guide wire or working catheter into proper position. As used herein the direction distal is used to refer to the direction closer to a patient in the intended use of the component and the term proximal is used to refer to the direction further away to a patient in the intended use of the component.

Figure 3:
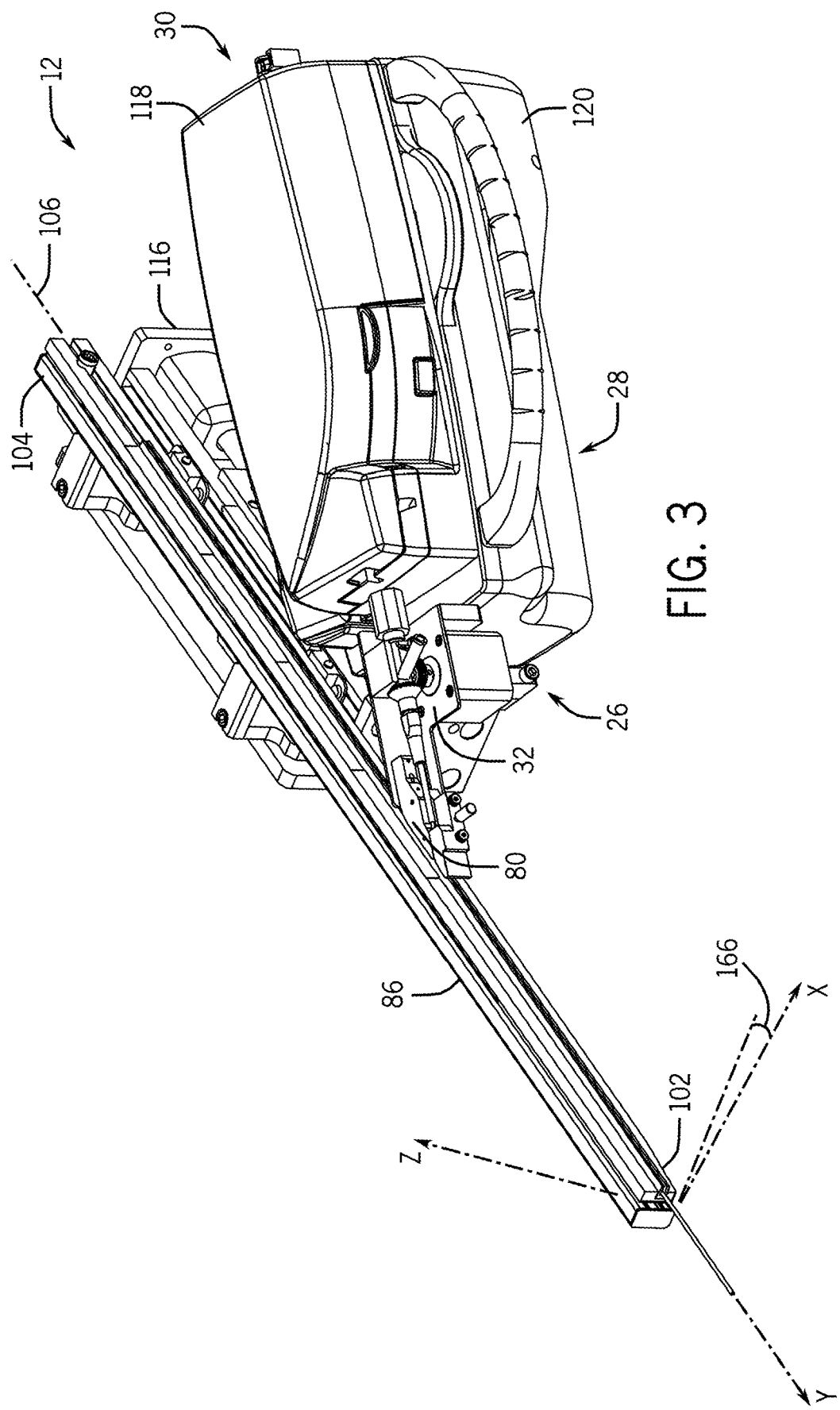
FIG. 3 is an isometric view of a catheter bedside system.

Referring to FIG. 3 bedside system 12 includes a guide catheter mechanism 26, a working catheter mechanism 28 and a guide wire mechanism 30. In one embodiment, working catheter mechanism 28 and guide wire mechanism 30 are of the type described in U.S. Pat. No. 7,887,549 entitled "Catheter System" which is incorporated herein in its entirety.

Figure 4:
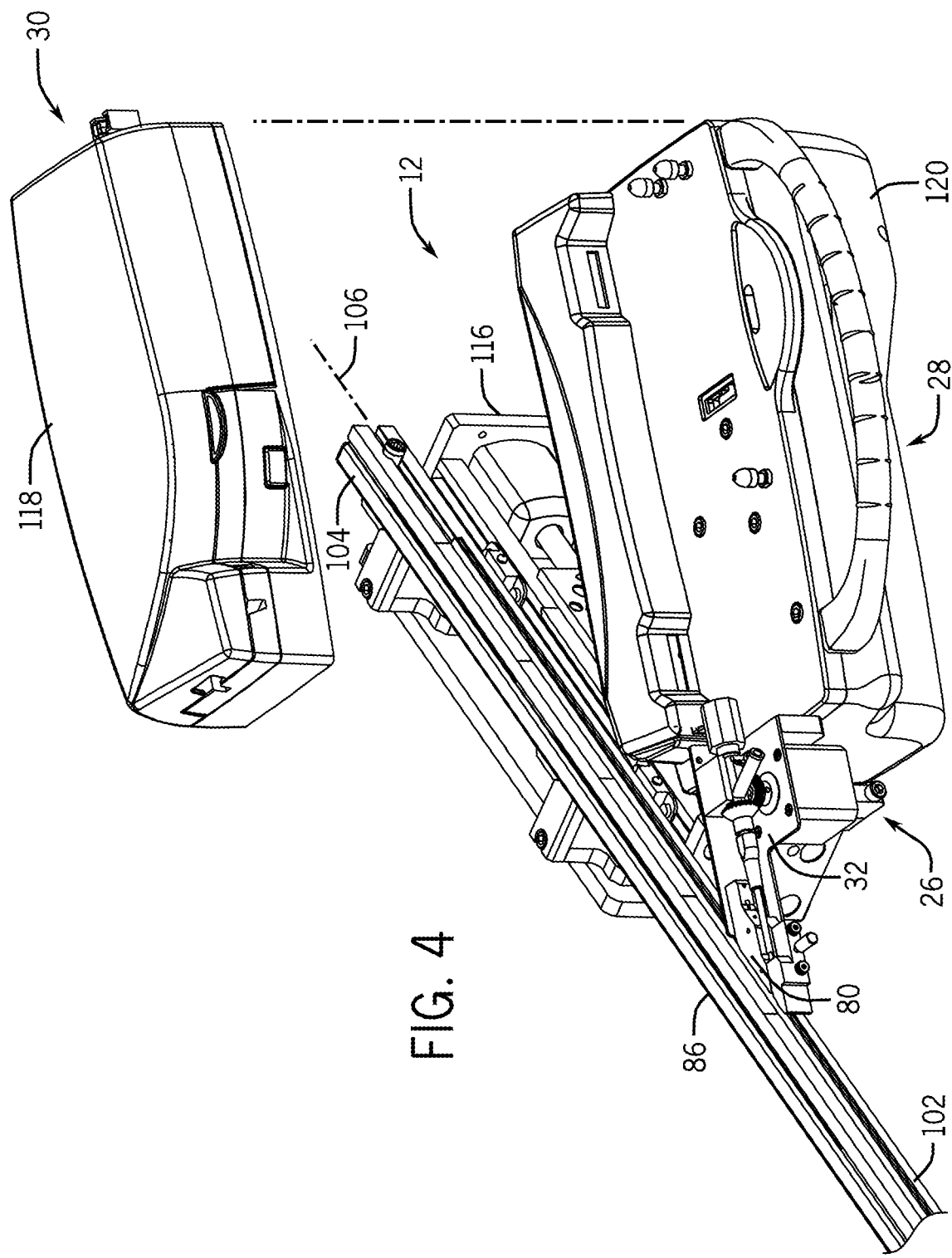
FIG. 4 is an isometric view of a catheter bedside system.
Figure 5:
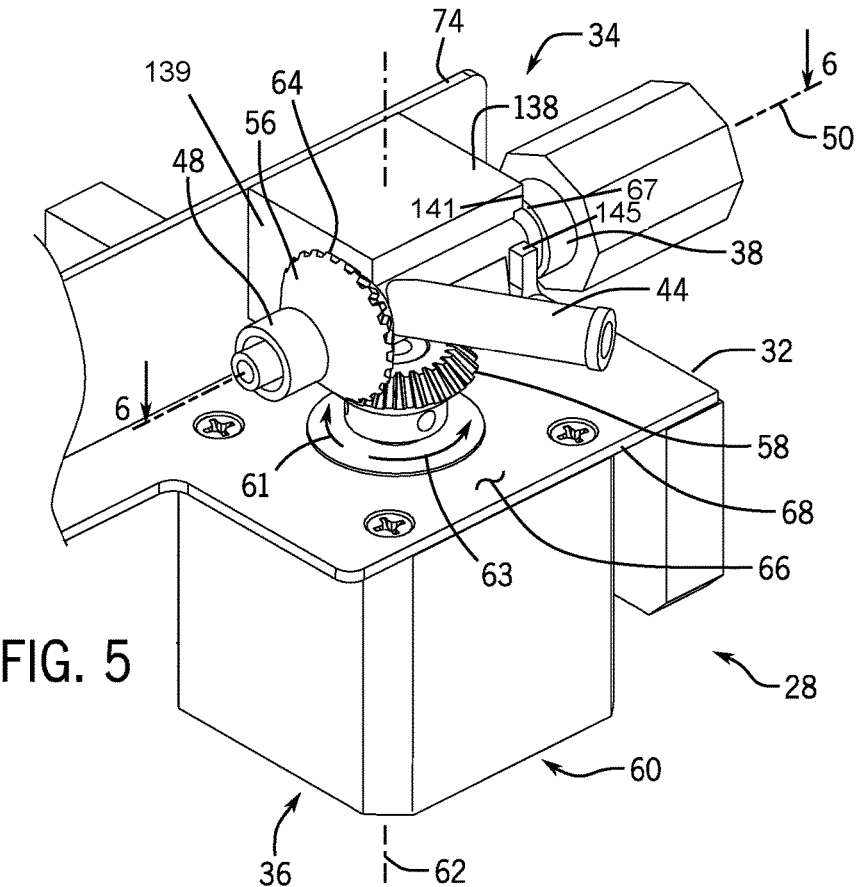
FIG. 5 is an isometric view of a hemostasis valve and guide catheter drive mechanism

Referring to FIGS. 3-5 guide catheter mechanism 26 includes a base 32 configured to releasably receive a hemostasis valve 34 and a guide catheter rotational drive 36. Base 32 may include a quick release mechanism to releasably secure hemostasis valve 34 to base 32. One embodiment of a guide catheter quick release is disclosed in US application publication US 2012/0179032 entitled "Remote Catheter System With Steerable Catheter" which is incorporated herein in its entirety.

Hemostasis valve 34 includes a first leg 38 having a distal end 40 and a proximal end 42. A second leg 44 extends from first leg 38 and is in fluid communication with first leg 38 such that a fluid may be introduced into a proximate end 46 of second leg 44. Hemostasis valve first leg 38 defines a longitudinal axis 50 extending from proximal end 42 of first leg 38 to distal end 40 of first leg 38.

The distal end 40 of first leg 38 includes a rotating luer connector 48 that is rotatably coupled to distal end 40 of first leg 38. Rotating luer connector 48 includes an external surface 52 and an internal region 54 having a luer female interface to releasably couple a guide catheter. Luer connectors are known in the art and provide a fluid tight connection between a guide catheter and a hemostasis valve. Luer connectors are covered by standards such as ISO 594 (including sections 594-1 and 594-2) and EN 1707.

In one embodiment external surface 52 of rotating luer connector 48 includes a driven member such as gear 56 that is driven by drive mechanism including a rotational drive 36. Rotational drive 36 includes a driven member such as a drive gear 58 operatively connected to a motor 60. Gear 56 may be integrally formed with rotating luer connector 48 and coupled with a drive gear 58 for rotational movement of the rotating connector. The driven member as described herein may include a beveled gear, a friction surface, or a surface configured to receive a belt and the drive member may include a beveled gear, a wheel, or a belt.

In another embodiment, gear 56 may be secured to the outer surface of rotational luer connector 48 such that gear 56 rotates along with the rotation of rotational luer connector 48 about longitudinal axis 50 of the first leg 38 of hemostasis valve 34.

Gears 56 and 58 may be beveled gears or miter gears to provide direct rotation of driven gear 56 from a shaft rotated by motor 60 and extending along an axis 62 perpendicular to longitudinal axis 50 of first leg 38 of hemostasis valve 34. Motor 60 rotates in a first direction 61 about axis 62 of the motor and an opposing second direction 63 about axis 62 of the motor. Referring to FIG. 1, gear 56 is beveled such that gear teeth 64 extend in a direction toward proximal end 42 and away from distal end 40 of first leg 38. Additionally, in one embodiment driven gear 56 is located a distance from distal end 40 to permit attachment and removal of a guide catheter from rotational luer connector 48. Drive gear 58 is positioned below first leg 38 to permit easy removal of the hemostasis valve 34 from base 32.

Motor 60 may be secured to base 32, such that drive gear 58 is located above a first surface 66 of base 32 and motor 60 is located below an opposing second surface 68 of base 32. First surface 66 being closer to first leg 38 than second surface 68 of base 32.

Figure 6:
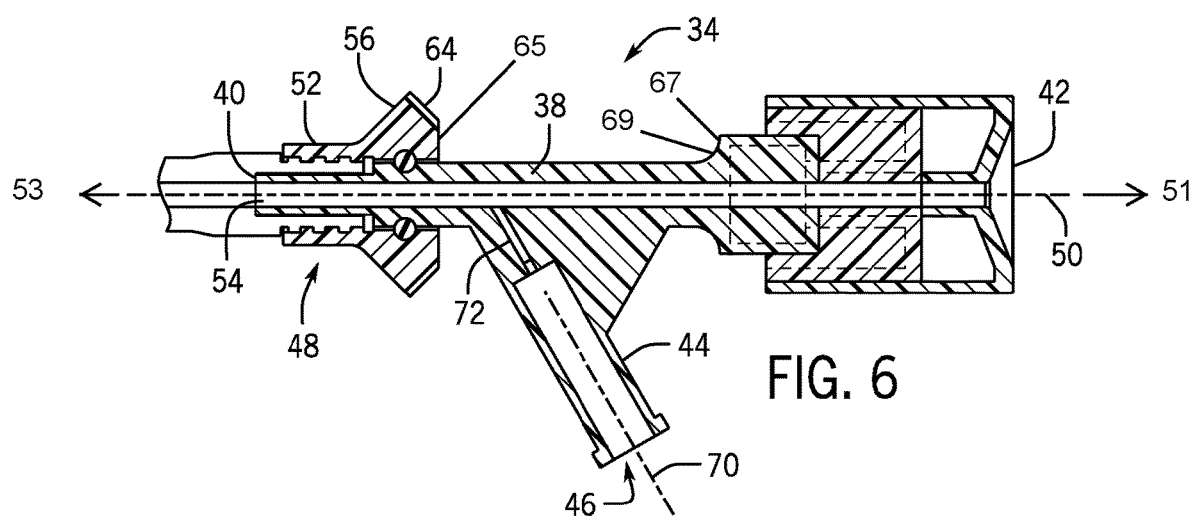
FIG. 6 is a cross-sectional view a hemostasis valve.

Referring to FIG. 1 FIG. 6 second leg 44 of hemostasis valve 34 has a longitudinal axis 70 extending longitudinally along second leg 44 from proximate end 46 to a distal end 72 adjacent first leg 38. A second leg working plane is defined by axis 50 of first leg 38 and axis 70 of second leg 44. In one embodiment hemostasis valve 34 is secured to base 32 such that the second leg working plane is not perpendicular to the horizontal as defined by gravity. Rather the second leg working plane forms an acute angle with respect to a vertical plane permitting an operator access to proximate end 46 of second leg 44. In one embodiment second leg working plane may be co-planer with a horizontal plane. As discussed above, hemostasis valve 34 may be releasably coupled to base 32 with a quick release that allows removal of hemostasis valve 34 from base 32.

Figure 14:
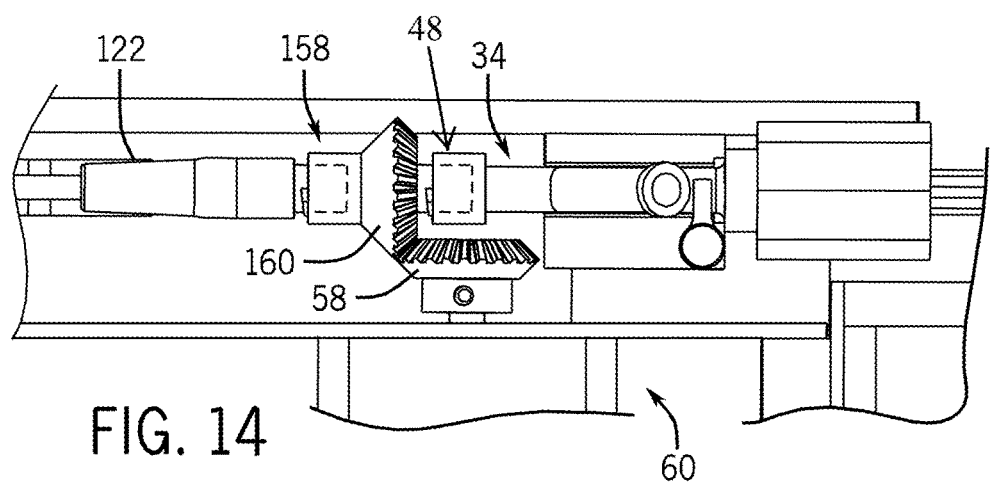
FIG. 14 is a partial side view of the hemostasis valve and guide catheter.

Referring to FIG. 5, base 32 includes a raised wall 74 extending upwardly from and perpendicular to surface 66. Wall 74 extends in a direction parallel to axis 50 of hemostasis valve 34, when hemostasis valve 34 is secured to base 32. Wall 74 is proximate a rear portion 76 of base 32 and distal a front portion 78 of base 32. Gear 58 being intermediate wall 74 and front portion 78 of base 32. A guide member 80 is secured to wall 74 and extends in a direction substantially parallel to axis 50 when hemostasis valve 34 is secured to base 32. Guide member 80 has a guide portion 82 configured to direct a portion of a guide catheter prior to the guide catheter entering a sleeve 84. Referring to FIG. 5 and FIG. 6, a first or distal linear bearing surface 139 is operatively connected to base 32 The distal linear bearing surface 139 contacts a rotatable linear bearing surface 65 prohibiting movement of the rotating connector 48 in a proximal direction 51 parallel to a valve body longitudinal axis colinear with axis 50. A second or proximal linear bearing surface 141 is operatively connected to base 32. Proximal linear bearing surface 141 contacts a linear bearing surface 67 on hemostasis valve 34. First leg 38 of hemostasis valve 34 includes a transition portion 69 to linear bearing surface 67. Referring to FIG. 6 transition portion 69 is arcuate. Base 32 contacts linear bearing surface 67 and does not contact the transition portion 69. Stated another way proximal linear bearing surface 141 contacts linear bearing surface 67 and does not contact transition portion 69. Distal linear bearing surface 139 and proximal linear bearing surface 141 interacts with linear bearing surface 65 and linear bearing surface 67 respectively to locate hemostasis valve 34 with respect to base 32 and aligns driven member 56 with drive member 58. Distal linear bearing surface 139 interacts with linear bearing surface 65 to prohibit movement of hemostasis valve 34 in proximal direction 51 which is the direction along axis 50 from the distal port toward the proximal port. Proximal linear bearing surface 141 interacts with hemostasis valve linear bearing surface 67 to prohibit movement of hemostasis valve 34 in a distal direction 53 which is the direction along axis 50 opposite the proximal direction 51. Rotatable linear bearing surface 65 is proximate to and rotates with driven member 56. A longitudinal slot having a longitudinal opening is defined by and extends from the distal linear bearing surface and the proximal linear bearing surface. Referring to FIG. 5 and FIG. 14 hemostasis valve 34 is positioned within longitudinal slot. A finger 145 proximate longitudinal slot prohibits movement of the hemostasis valve in a direction perpendicular to longitudinal axis 50 from longitudinal slot through the longitudinal opening.

Referring to FIG. 3 and FIG. 10 a track 86 includes a channel 88. A set screw 90 or other type of fastener extends through track 86 into channel 88 to secure sleeve 84. In one embodiment sleeve 84 includes a first wall 92 and a second wall 94 and a third wall 96 extending from first wall 92 forming a cavity 98. An opening 100 is defined as the space between the two free ends of second wall 94 and third wall 96. In another embodiment, sleeve 84 may be formed by a single arcuate wall member having an opening 100. A disposable sterile barrier sleeve such as a plastic sleeve may be located about track 86 such that when sleeve 84 is isolated from track 86. Sleeve 84 may be a single use device and disposed of once a medical procedure using the sleeve is complete. In another embodiment, no sleeve 84 is placed into channel 88, rather a sterile barrier may be placed within channel 88 to isolate a guide catheter from the walls of channel 88. In an alternative embodiment, no sleeve or sterile barrier is employed and track 86 is a single use device that is discarded after use and replaced prior to the use of the bedside system with another patient or for another procedure.

Referring to FIG. 7 and FIG. 8 track 86 includes a distal end 102 that is configured to be located proximate a patient, and an opposing proximal end 104. A track longitudinal axis 106 is defined by the longitudinal axis of the track 86 extending between proximal end 104 and distal end 102. In one embodiment track longitudinal axis 106 and hemostasis valve longitudinal axis 50 form an acute angle 108. In one embodiment angle 108 is preferably between 25 and 45 degrees, and more preferably between 30 and 45 degrees. In one embodiment angle 108 is 30 degrees.

In one embodiment plane track longitudinal axis 106 forms an acute angle 112 with a horizontal plane defined by gravity that also represents the horizontal plane of a bed or procedural surface that a patient lies on. Track longitudinal axis 106 and hemostasis valve first leg longitudinal axis 50 form a plane 110. In one embodiment plane 110 is at an acute angle 108 with respect to the horizontal plane. In other embodiments, the angle formed between plane 110 and the horizontal may be an acute angle different than the angle formed by track longitudinal axis 106 and the horizontal plane.

Referring to FIGS. 7 and 8 guide catheter mechanism 26 is offset to one side of track 86, as a result plane 110 is not perpendicular to the horizontal plane. In one embodiment guide catheter mechanism 26 is located closer to an operator than track 86. Stated another way, when an operator operates guide catheter mechanism 26 the operator will be closer to the guide catheter mechanism than the track.

Referring to FIG. 3, in one embodiment, track 86, guide catheter mechanism 26 and cassette 118 may be rotated downwardly about axis y such that guide catheter mechanism 26 and cassette 118 are easier to access by an operator facing guide catheter mechanism 26 and cassette 118. In one embodiment, the vector shown as x is perpendicular to the longitudinal axis 106 extends through channel 88 and forms an angle 166 below a horizontal plane. In one embodiment angle 166 is 15 degrees below a horizontal plane as defined by gravity. In one embodiment an operator is located proximate a first side a patient's bed. A support is located on one side of the bed typically opposite the first side. The cassette 118 and guide catheter mechanism 26 is closer to the first side of the patient's bed than track 86. In this way, the operator or physician has easy access to the cassette 118 and guide catheter mechanism 26. By tilting the cassette 118 and guide catheter mechanism downwardly toward the patient's bed such that the portion of the cassette 118 and guide catheter mechanism 26 closer to track 86 is higher vertically than the portion of the cassette 118 and guide catheter mechanism 26 that is furthest from track 86. Additionally, by pivoting guide catheter mechanism 26 and cassette 118 from the longitudinal axis 106 by angle 108, the guide catheter mechanism and cassette 118 is located in a position that allows for access by the operator and/or physician.

Track 86 is secured to a bedside support 114 and is maintained in a fixed position relative to patient bed 22. Bedside support 114 may be secured directly to a side of patient bed 22 or may be secured to a floor mounted support that is either fixed relative patient bed 22 or positioned on a floor proximate patient bed 22 such that track 86 is in a fixed location with respect to patient bed 22 or to a patient on patient bed 22 during a catheter based procedure. In one embodiment, the orientation of track 86 may be adjusted with respect to patient bed 22 so that angle 112 may be adjusted as well. In another embodiment angle 112 may be between ten degrees and forty five degrees and in one embodiment angle 112 may be thirty degrees.

Figure 12:
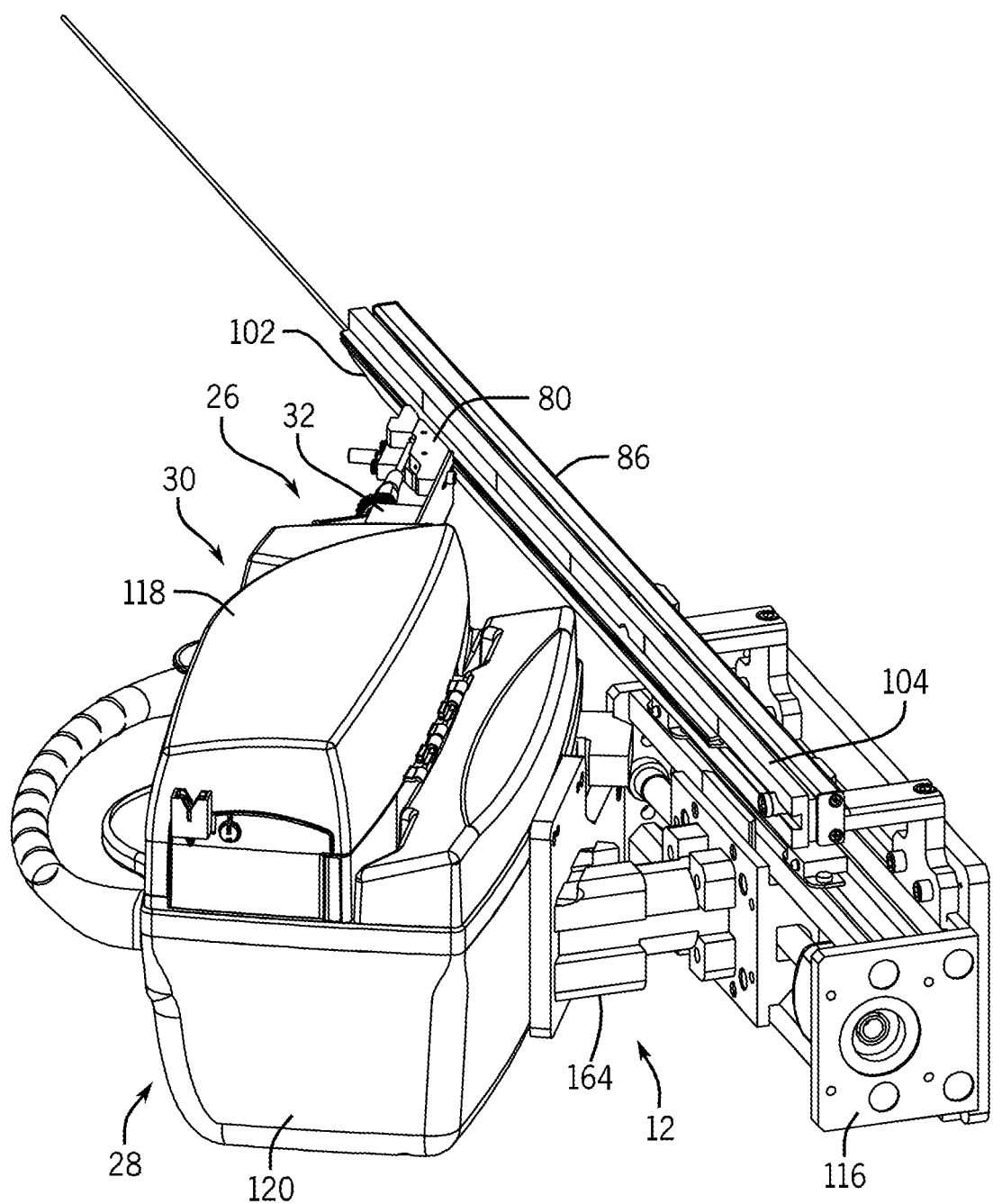
FIG. 12 is a rear isometric view of the catheter bedside system.

Referring to FIG. 12 guide catheter mechanism 26 may be secured to a linear actuator 116 to translate guide catheter mechanism along an axis parallel to or co-linear with track axis 106. The linear actuator 116 may provide for discrete incremental movement or may provide for continuous movement. In one embodiment the linear actuator includes a rack and pinion and in another embodiment includes a robotic arm. Linear actuator 116 moves independently of track 86. As discussed above working catheter mechanism 28 and guide wire mechanism 30 may be included in a cassette 118 that is operatively removably secured to a base member 120. Base member 120 and guide catheter mechanism 26 may be operatively secured to linear actuator 116 with a support 164, such that guide catheter mechanism 26, working catheter mechanism 28, and guide wire mechanism 30 are translated together along a linear axis.

The operation of the guide catheter mechanism 26 during a catheter procedure will now be described using an exemplary embodiment. A patient in need of a catheter based procedure will lie in a supine position on patient bed 22. An opening in the femoral artery will be prepared for the introduction of a guide catheter 122.

Track 86 will be positioned relative to the patient such that distal end 102 of track 86 is located proximate the femoral artery of the patient. Track 86 is covered with a sterile barrier and a single used sleeve 84 is positioned in channel 88. Typically track 86 will be covered with a sterile barrier prior to positioning relative to the patient. As sleeve 84 is positioned in channel 88 the sterile barrier is placed into channel 88 such that the sterile barrier provides a guard against any fluids that may be exposed on sleeve 84 from contacting track 86. Sleeve 84 has a distal end 124 and a proximal end 126. Distal end 124 of sleeve 84 is located proximal distal end 102 of track 86. In one embodiment, sleeve 84 may have certain geometry to provide for placement within channel 88 of track 86 and to facilitate entry and removal of a portion of guide catheter 122.

In one catheter procedure on the heart of a patient, a guide catheter 122 of appropriate length is selected based on the size of the patient. Guide catheter 122 has a proximal end 128 and a distal end 130. In one embodiment, proximal end 128 is first connected to rotating luer connector 48 of hemostasis valve 34. Distal end 130 is then manually inserted into the femoral artery of the patient and positioned such that distal end 130 of the guide catheter 122 is located adjacent the ostium of the heart. It is also contemplated that proximal end 128 of guide catheter 122 may be connected to rotating luer connector 48 after distal end 130 is positioned adjacent the ostium.

Once guide catheter 122 is properly positioned relative to the patient's heart, a central portion 132 of guide catheter 122 located outside of the patient is placed within sleeve 84 by pushing a central portion 132 of guide catheter 122 through opening 100 into cavity 98.

Figure 11:
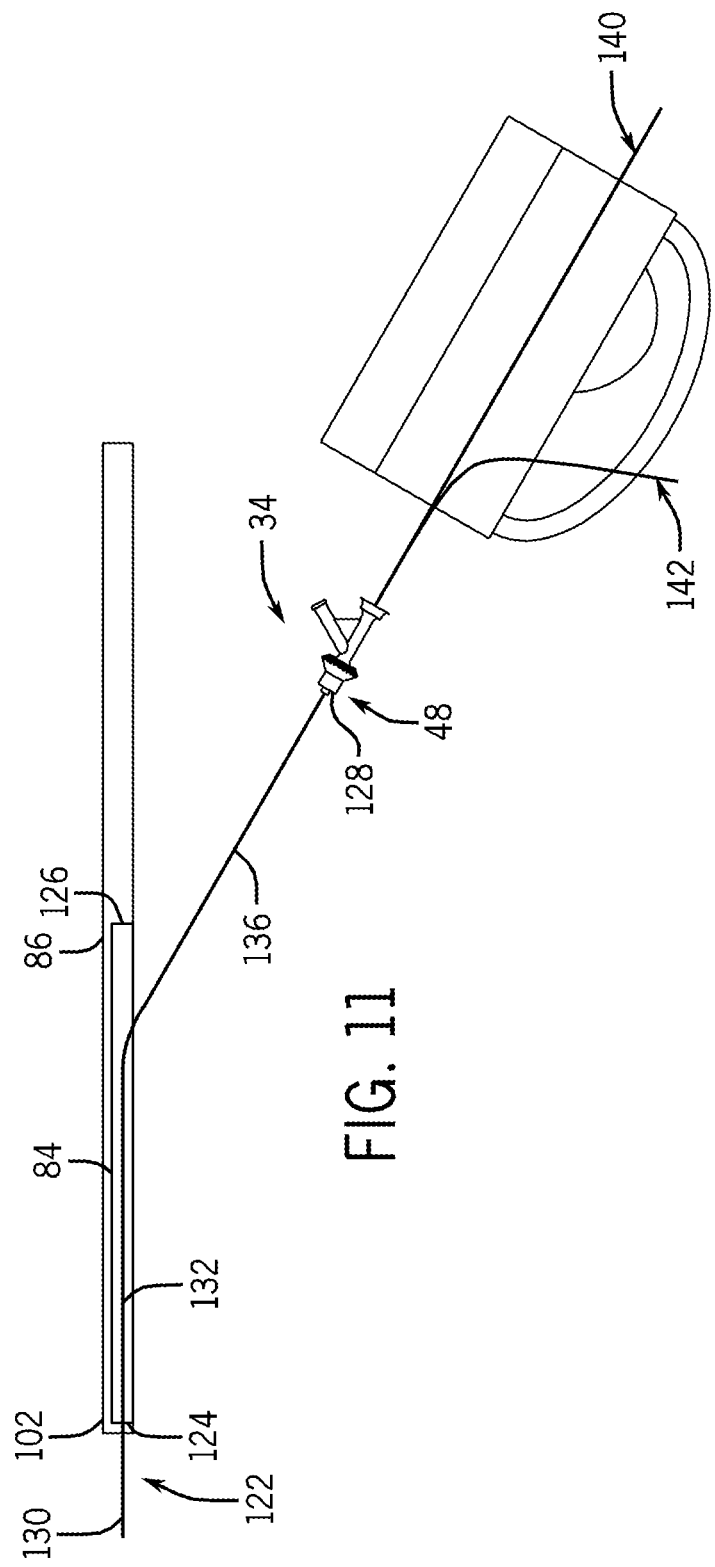
FIG. 11 is a top schematic view of the hemostasis valve, guide wire, working catheter, and guide catheter.

Referring to FIG. 9 and FIG. 11, an entering portion 134 of guide catheter 122 will be exposed between distal end 102 of track 86 and the patient. Additionally, a connecting portion 136 adjacent proximal end 124 of guide catheter 122 extends outwardly from sleeve 84 and track 86 in a direction toward guide catheter mechanism 26. In one embodiment, connecting portion 136 has sufficient length to allow for the guide catheter hub to be connected to rotating luer 52 and have sufficient length to bend into track 86. Connecting portion 136 extends outwardly from sleeve 84 at angle between approximately 25 to 45 degrees and 30 in but may be between 30 and 45 degrees and may be 30 degrees. Guide portion 82 guides guide catheter from support 80 into track 86. Guide portion 82 may include a curved surface to assist in the transition of the guide catheter into track 86.

Proximal end 128 guide catheter 122 is connected to rotating luer connector 48. In one embodiment, proximal end 128 of guide catheter 122 is connected to rotating luer connector 48 of hemostasis valve 34 prior to distal end 124 of catheter 122 being inserted into the patient or prior to central portion 132 being positioned within sleeve 84. Hemostasis valve 34 is secured to base 32 with a quick release mechanism 138 such that driven gear 56 is engaged with drive gear 58. Driven gear 56 located on external surface 52 of rotating luer connector 48 is moved in a direction toward drive gear 58 to engage driven gear 56 with drive gear 58. Quick release 138 is then closed to releasably capture hemostasis valve 34. In an engaged position proximal end 46 of second leg 44 of hemostasis valve extends away from track 86 and having a horizontal vector component. Stated another way in a preferred embodiment, second leg working plane defined by axis 50 of first leg 38 and axis 70 of second leg 44 does not define a plane that is perpendicular to a horizontal plane defined by gravity or by a horizontal plane defined generally by the top surface of the patient's bed 22.

Guide Catheter mechanism 26 is moved linearly by linear actuator 116 to allow proper alignment of proximal end 126 of guide catheter 122 with guide catheter mechanism 26. Guide catheters are typically sold with varying lengths and selected depending on the size of the patient. However, since the length of the guide catheter required varies from patient to patient, it may be necessary to adjust the position of the hemostasis valve quick release for each patient. In one embodiment hemostasis valve quick release may be adjusted along an axis parallel to track axis 106 relative to base 32. In another embodiment, base 32 may be moved along an axis parallel to track axis 106 to properly position hemostasis valve 34 so that guide catheter 122 is properly positioned relative to the patient.

Linear adjustment of hemostasis valve along an axis parallel to track axis 106 may be done manually or may be controlled by user interface 18 at work station 14 that is typically remote from bedside system 12. Work station 14 communicates with bedside system through a wireless or wired connection. In this embodiment, an operator manipulates user interface 18 such as a joy stick or touch screen to provide a control signal to a linear actuator motor to move base 32 relative to track 86.

Once guide catheter 32 is secured to hemostasis valve 34 and hemostasis valve 34 is secured to base 34 with quick release 138 a guide wire 140 and/or working catheter 142 is introduced into the proximal end 42 of first leg 38. Proximal end 42 of first leg 38 includes a valve member 162 such as a Tuohy Borst adapter. Tuohy Borst adapters are known in the art and operate to adjust the size of the opening in proximal end 42 of first leg 38 of hemostasis valve 34 to minimize the risk that fluids may exit the proximal end 42 of first leg 38. Other types of adapters known in the art may also be used with hemostasis valve 34 to adjust the size of the opening in proximal end 42 of first let 38.

During a catheter procedure it may be necessary to reseat distal end 124 of guide catheter 122 within the ostium of the patient. An operator may rotate guide catheter 122 by providing a control signal to motor 60 to rotate drive gear 58 in a clockwise or counterclockwise direction. As a result driven gear 56 rotates causing rotation of rotating luer connector 48 and rotation of guide catheter 122. In addition to a requirement to rotate guide catheter 122 it may also be necessary during a catheter procedure to move guide catheter 122 along track axis 106 to properly position distal end 124 of guide catheter 122. Work station may also include a user interface such as a joy stick, button, touch screen or other user interface to control a linear actuator to move guide catheter mechanism 26 in a direction substantially parallel to track axis 106. Movement in a first direction in parallel to track axis will result in movement of guide catheter 122 further into the patient and movement of the linear translator in an opposing second direction will result in movement of guide catheter 122 outwardly from the patient.

If an operator wishes to remove guide catheter 122, working catheter 142 and/or guide wire 140 during a catheter procedure, the operator releases quick release 138 and removes hemostasis valve 34 along with guide catheter 122 and working catheter 142 and/or guide wire 140. Central portion 132 of guide catheter 122

Working catheter 142 and guide wire 140 may be removed from their respective working catheter mechanism 28 and guide wire mechanism 30 as described in U.S. Pat. No. 7,887,549. Once guide catheter 122, 140 hemostasis valve 34, working catheter 142 and guide wire 140 are removed from guide catheter mechanism 26, working catheter mechanism 28 and guide wire mechanism 30 an operator may manipulate guide catheter 122, working catheter 142 and guide wire 140 manually.

Figure 13:
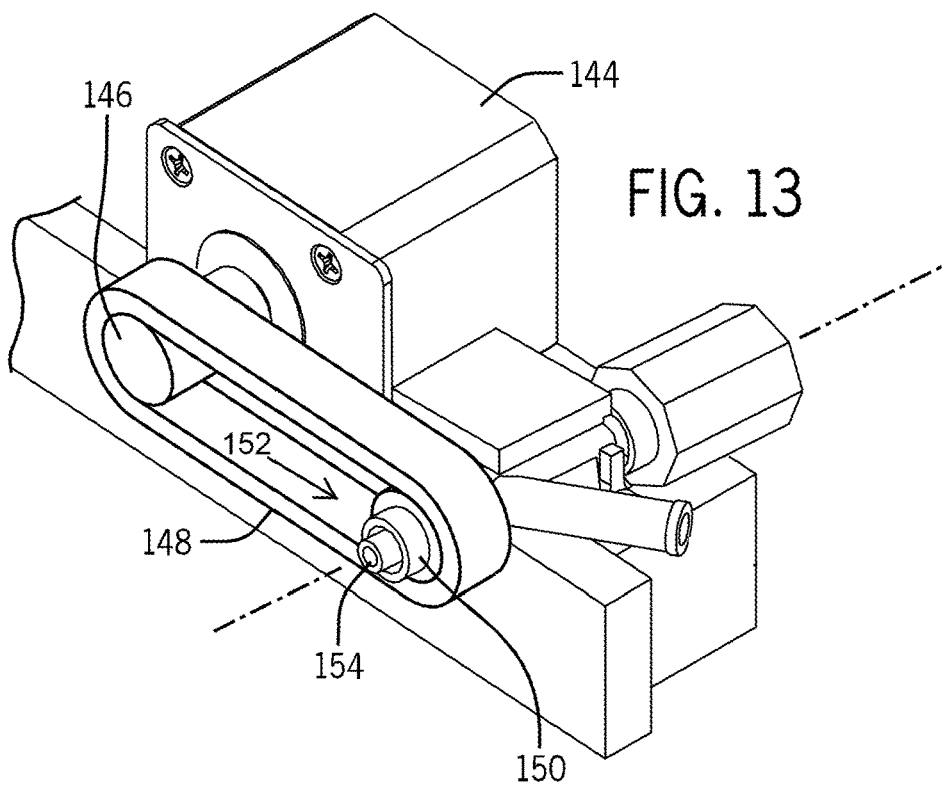
FIG. 13 is an alternative hemostasis valve and guide catheter drive mechanism.

Referring to FIG. 13 an alternative embodiment of a drive for rotational luer connector includes a motor 144 rotating a first pulley 146 driving a belt 148 such as a timing belt. Belt 148 is connected to the outer surface 150 of a pulley 152 about the outer surface 150 of a rotational luer connector 156. First pulley 146 may include a plurality of teeth that mesh with ribs on belt 148 and the outer surface 150 of rotational luer connector 154 also include a plurality of teeth that mesh with ribs on belt 148. In this manner control of motor 144 allows for controlled rotation in a clockwise and counterclockwise of rotational luer connector 156 thereby rotating guide catheter 122 attached thereto. In one embodiment pulley 152 and bevel gear 56 are integrally formed with the outer surface of rotating luer connector. However, it is also contemplated that a collet having an outer surface defining a pulley or bevel gear may be secured to the outer surface of rotating luer connector.

Referring to FIG. 14, in another embodiment, a luer extension member 158 may act to connect proximal end 128 of guide catheter 122 to rotating luer connector 48. Luer extension member 158 may include an outer surface having a gear 160 or pulley member to be operatively connected to the rotational drive motor 60 via drive gear 58. In this embodiment, the rotational drive motor is operatively coupled to the outer surface of luer extension member and not directly to the outer surface of the rotating luer connector. This permits the use of presently available commercially available hemostasis valves. Additionally in a further embodiment a luer extension member may include a rotating portion such that the distal end of the hemostasis valve need not have a rotational luer connector but rather include a non-rotational luer connector. Extension 158 includes a female luer connector on the distal end to removably receive a male luer fitting on a guide catheter. Extension 158 also includes a male luer connector on the proximal end that is removably received within a female luer connector of a rotating connector on a Hemostasis valve. Note that in one embodiment, gear 160 is a beveled gear with teeth facing the proximal end.

Figure 15:
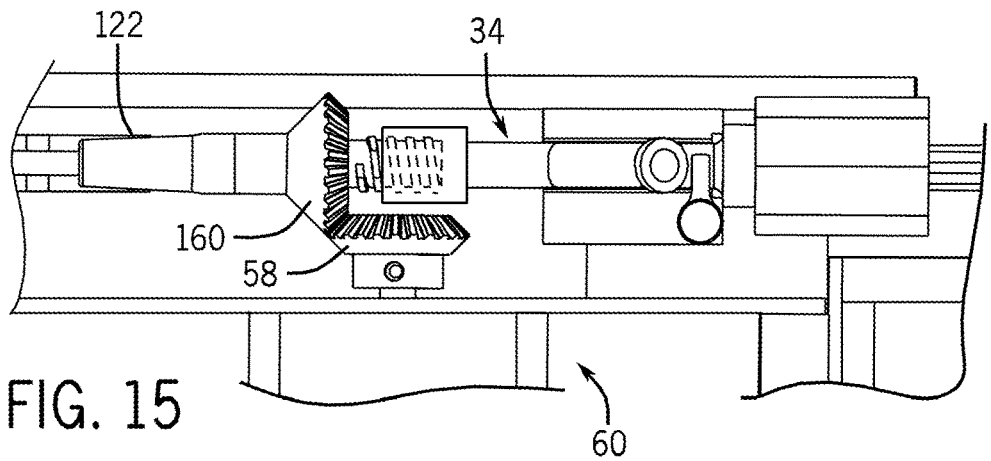
FIG. 15 is a partial side view of an alternative guide catheter hub and guide catheter drive mechanism.
Figure 16:
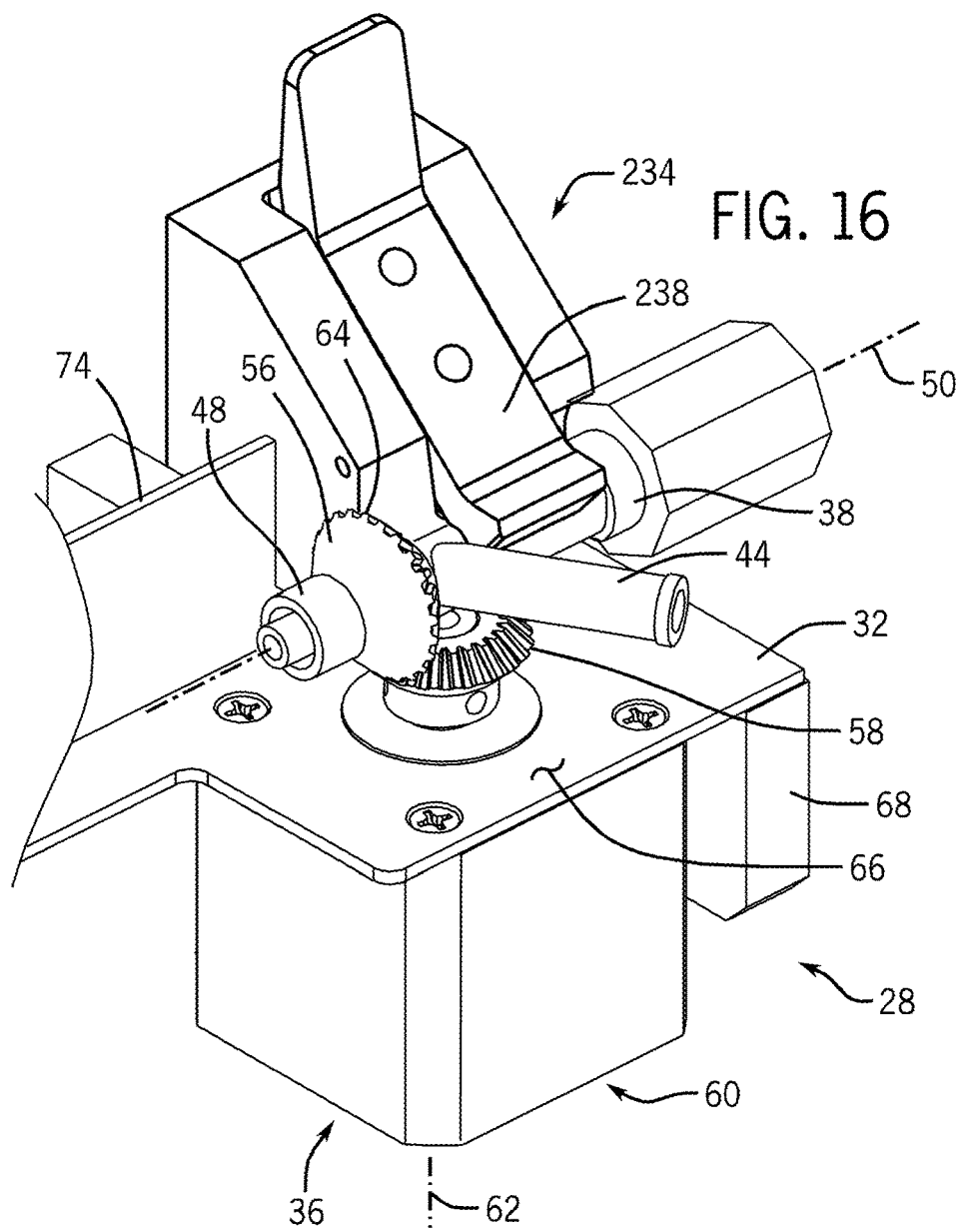
FIG. 16 is an isometric view of a quick release for a hemostasis valve.
Figure 17:
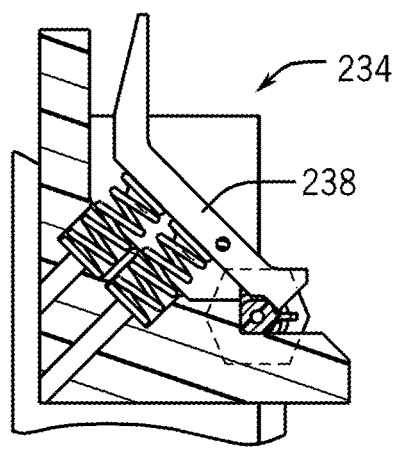
FIG. 17 is a cross sectional view of a portion of the quick release of FIG. 16. in an engaged position.
Figure 18:
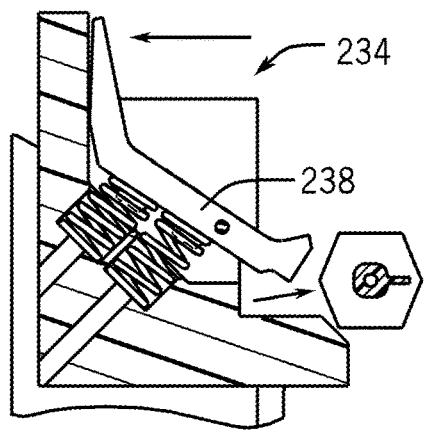
FIG. 18 is a cross sectional view of a portion of the quick release of FIG. 16. in a disengaged position.

Referring to FIG. 15 in another embodiment, a hub of guide catheter 122 may have gear formed therewith or attached thereto to connect to a rotating luer of hemostasis valve 34. Referring to FIG. 16-FIG. 18 a release 234 includes a lever 238 that releasably engages hemostasis valve 34.

Figure 19:
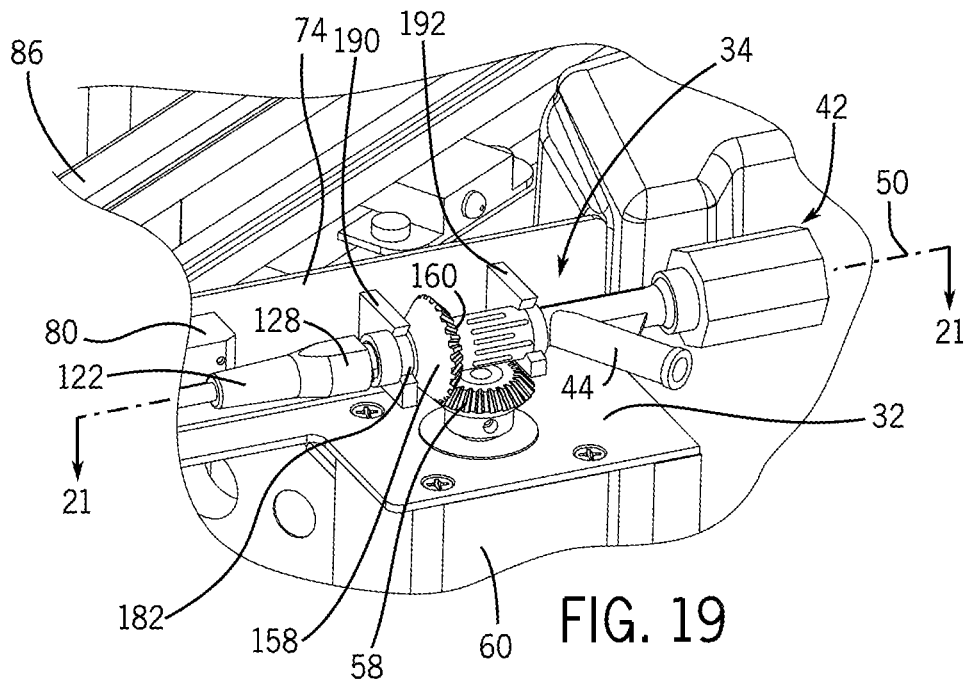
FIG. 19 is an isometric view of an extension member rotatably coupling a male rotating luer lock of a hemostasis valve which is affixed to the base which carries a drive member.

Referring to FIG. 19, an extension member 158 is interposed between a Y-connector or hemostasis valve 34 and a guide catheter 22. This extension member 158 interacts with the drive gear 58, the guide catheter 122 and the Y-connector or hemostasis valve 34 to impart rotation to the guide catheter 122 while isolating the valve 34 from rotational motion such that the position of the second leg 44 of the valve 34 does not change position when the guide catheter 122 is rotated. The bracket 190 interacts with the groove 182 in the extension member 158 to provide it support as it rotates and is itself secured to either base 32 or wall 74. The valve 34 is supported by bracket 192 that is itself secured to either base 32 or wall 74. The two brackets 190 and 192 provide stability to the longitudinal axis 50 of the valve 34. The proximate end 128 of the guide catheter 122 provides a luer interlock with the extension member 158. Guide member 80 and track 86 provide support for the guide catheter 122 as it extends in the distal direction away from the extension member 158 and toward the patient bed 22 shown in FIG. 2. The extension member 158 is provided with a beveled gear face 160 which can be rotated by the drive gear 58 to impart rotation to the guide catheter 122, although other means can be used to impart rotation to the extension member 158, such as that illustrated in FIG. 22. The drive gear 58 is in turn rotated by motor 60.

Figure 20:
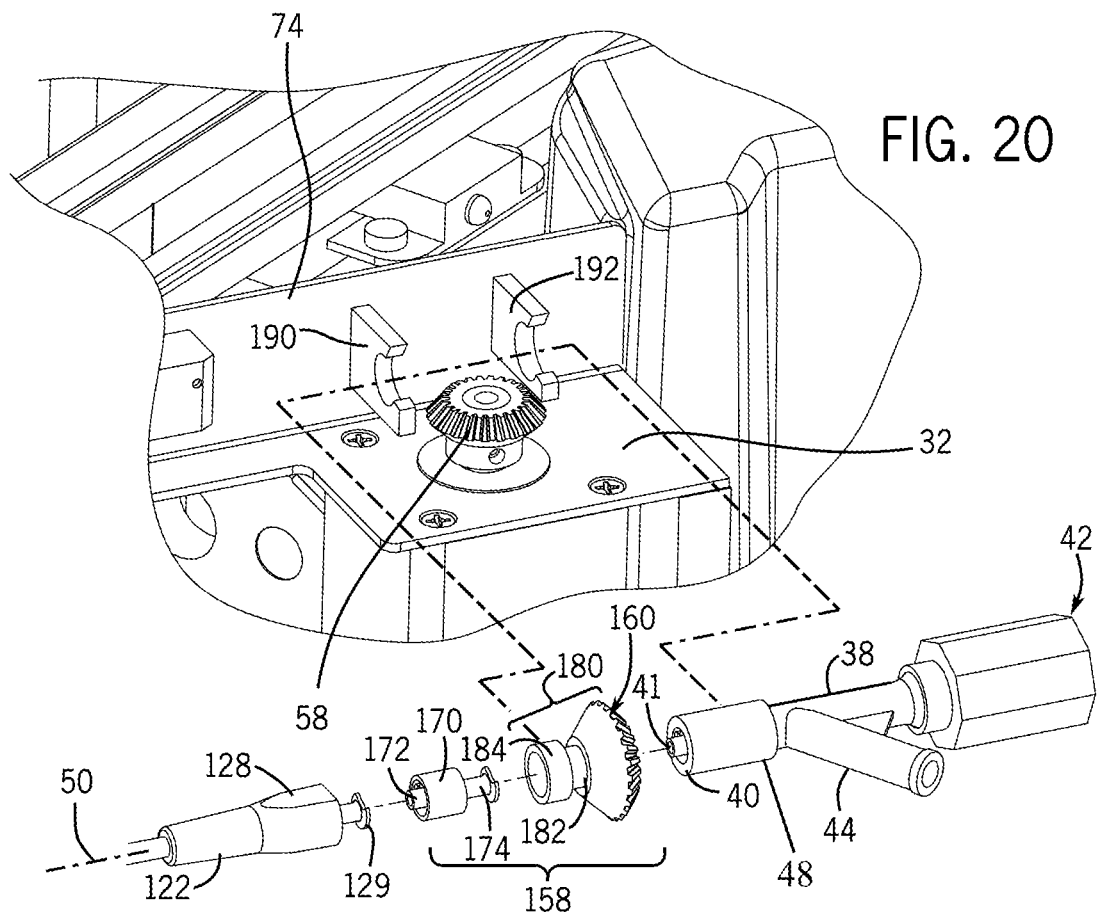
FIG. 20 is an exploded view of the guide catheter, extension member and hemostasis valve of FIG. 19.

Referring to FIG. 20, the extension member 158 may be composed of an inner piece 170 and an outer piece 180. The inner piece 170 has a male luer lock 172 that interacts with receptacle 129 on the guide catheter 128 to provide a fluid tight connection. It also has a female luer lock that forms a rotational fluid tight seal with protuberance 41 on the valve 40. Piece 170 is frictionally captured by the bore of outer piece 180 that has a collar 184 that helps to define the groove 182 that interacts with the bracket 190. Outer piece 180 also carries the beveled gear face 160. The frictional capture of inner piece 170 is such that outer piece 180 can readily transfer rotational motion to it. Alternatively, inner piece 170 and outer piece 180 could be molded as a single article.

Figure 21:
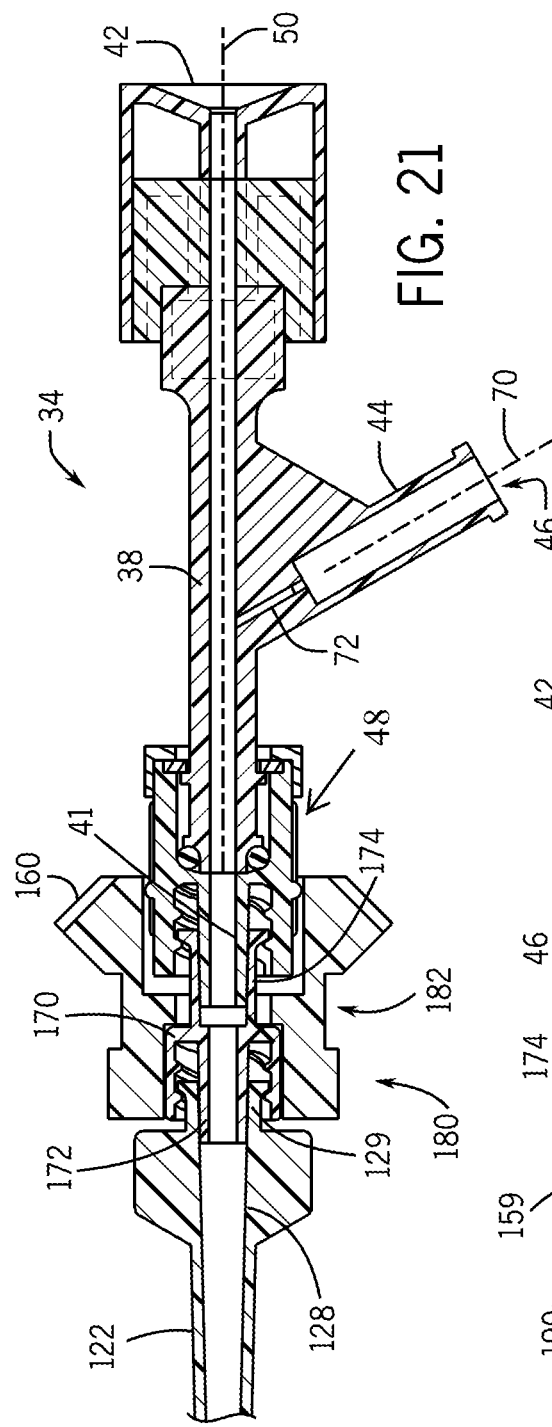
FIG. 21 is a cross-sectional view of FIG. 19 taken generally along line 21-21.

Referring to FIG. 21, the composite structure of guide catheter 122, extension member 158 and valve 34 is shown along section line 21-21 of FIG. 19. The second leg 44 of the valve 34 has a proximal end 46, a distal end 72 and a longitudinal axis 70. Inner piece 170 is nested inside the bore of outer piece 180. Male luer lock 172 engages the receptacle 129 at the proximal end 128 of the guide catheter 122 while female luer lock 174 forms a fluid tight rotational seal with the protuberance 41 on the distal end 40 of the valve 34. There is a continuous fluid path from the proximate end 42 of the valve 34 to the bore of the guide catheter 122.

Figure 22:
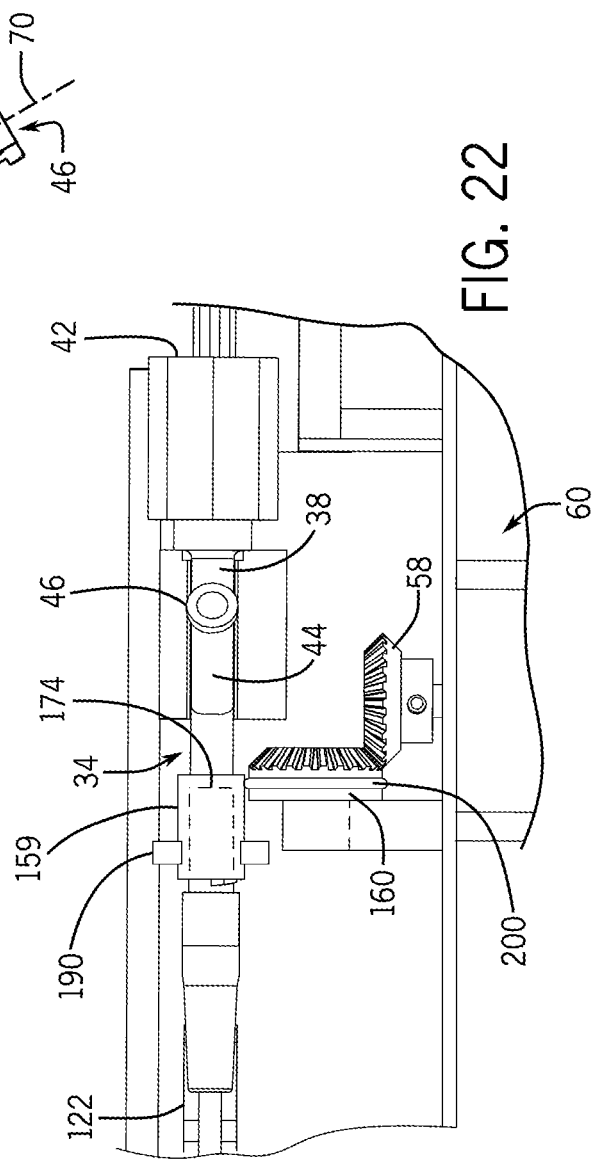
FIG. 22 is another embodiment of a friction drive member driving an outer surface of a rotating male luer lock of the hemostasis valve.

Referring to FIG. 22, an alternative extension member 159 can be used to impart rotational motion to the guide catheter 122 without carrying gear teeth. The drive gear 58 drives gear 160 that frictionally engages the outer surface of the extension member 159 with an O-Ring 200. The gear 160 could carry any means of frictional transfer to interact with the alternative extension member 159. The extension member 159 has a male luer lock 174 that engages the valve 34 to form a rotational seal.

Further modifications and alternative embodiments of various aspects of the invention will be apparent to those skilled in the art in view of this description. Accordingly, this description is to be construed as illustrative only. The construction and arrangements, shown in the various exemplary embodiments, are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The features described herein may be combined in any combination and such combinations are contemplated. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. An apparatus, comprising:
a hemostasis valve including a valve body having a proximal port, a distal port and a lumen extending between the proximal port and the distal port, at least one valve being located in the lumen to permit an interventional device to be passed therethrough, a rotating connector rotatably connected to the distal port configured to secure a catheter thereto, the rotating connector having a rotating linear bearing surface and a driven member configured to be rotatably driven by a drive mechanism, the catheter rotatingly coupled with the rotating connector;
the valve body having a valve body longitudinal axis extending through the proximal port and distal port; and
a base having a first linear bearing surface contacting the rotating linear bearing surface prohibiting movement of the rotating connector in a direction parallel to the valve body longitudinal axis.

2. The apparatus of claim 1, wherein the driven member is a hollow connector having a lumen receiving a female connector removably coupled to the rotating connector which is a male connector, the female connector extending from the catheter.

3. The apparatus of claim 2, wherein the male connector is a male luer connector and the female connector is a female luer connector.

4. The apparatus of claim 1, wherein the driven member includes a gear, and the rotating linear bearing surface rotates with the driven member and is proximate to the driven member.

5. The apparatus of claim 4, wherein the gear is a beveled gear having a plurality of teeth facing toward the proximal port.

6. The apparatus of claim 4, wherein the gear and the rotating connector are integrally formed as a single component.

7. The apparatus of claim 4, wherein the gear is removably coupled to the rotating connector.

8. The apparatus of claim 1, further including a bracket configured to receive a surface of the valve body.

9. The apparatus of claim 1, wherein the at least one valve includes a resilient material defining an opening, the resilient material being configured to deform and form a seal around the interventional device that is extending through the opening and through the lumen.

10. The apparatus of claim 1, wherein the base includes a second linear bearing surface interacting with a linear bearing surface on the hemostasis valve prohibiting movement of the rotating connector in a distal direction parallel to the valve body longitudinal axis.

11. The apparatus of claim 10, wherein the first linear bearing surface is proximal to the second linear bearing surface.

12. An apparatus comprising:
a hemostasis valve including a valve body with a first leg having a proximal port, a distal port and a lumen extending between the proximal port and the distal port, at least one valve being located in the lumen adjacent the proximal port to permit an interventional device to be passed therethrough, the valve body including a second leg extending at an angle relative to the first leg and in fluid communication with the first leg, a rotating connector rotatably connected to the valve body proximate the distal port, the rotating connector having a driven member and a rotating linear bearing surface, the valve body having a valve body longitudinal axis extending through the proximal port and distal port;
a catheter, releasably coupled to the rotating connector, the catheter having a catheter longitudinal axis;
a drive mechanism having a drive member removably interfacing with the driven member, and a motor operatively connected to the drive member, the motor rotating the catheter about the catheter longitudinal axis in a first direction and opposing second direction in response to rotation of the motor in a first direction about an axis of the motor and an opposing second direction about the axis of the motor, through rotation of the drive member, driven member and rotating lock connector; and
a base having a first linear bearing surface contacting the rotating linear bearing surface prohibiting movement of the rotating connector in a direction parallel to the valve body longitudinal axis.

13. The apparatus of claim 12, wherein the driven member includes a gear, and the rotating linear bearing surface rotates with the driven member and is proximate to the driven member.

14. The apparatus of claim 13, wherein the gear is a beveled gear having a plurality of teeth facing toward the proximal port, the drive member including a gear having a plurality of teeth operatively engaged with the plurality of teeth of the driven member.

15. The apparatus of claim 12, wherein the rotating lock connector is a rotating male luer lock connector.

16. The apparatus of claim 12, wherein rotation of the motor includes rotation of a motor shaft.

17. The apparatus of claim 12, wherein the base includes a second linear bearing surface interacting with a linear bearing surface on the hemostasis valve prohibiting movement of the rotating connector in a distal direction parallel to the valve body longitudinal axis.

18. The apparatus of claim 17, wherein the first linear bearing surface is proximal to the second linear bearing surface.

* * * * *